United States Patent
Alves Ferreira et al.

(10) Patent No.: US 10,704,055 B2
(45) Date of Patent: Jul. 7, 2020

(54) USE OF THE COFFEE HOMEOBOX GENE CAHB12 TO PRODUCE TRANSGENIC PLANTS WITH GREATER TOLERANCE TO WATER SCARCITY AND SALT STRESS

(75) Inventors: Marcio Alves Ferreira, Rio de Janeiro (BR); Fernanda Pinheiro Da Cruz Waltenberg, Rio de Janeiro (BR); Eduardo Romano De Campos Pinto, Asa Norte (BR); Maria Fatima Grossi De Sa, Asa Norte (BR)

(73) Assignees: UNIVERSIDADE FEDERAL DO RIO DE JANEIRO, Rio de Janeiro (BR); EMPRESA BRASILEIRA DE PESQUISA AGROPECUARIA—EMBRAPA, Plano, Piloto (BR)

( * ) Notice: Subject to any disclaimer, the term of this patent is extended or adjusted under 35 U.S.C. 154(b) by 1018 days.

(21) Appl. No.: 13/884,789

(22) PCT Filed: Nov. 8, 2011

(86) PCT No.: PCT/BR2011/000412
§ 371 (c)(1),
(2), (4) Date: Aug. 26, 2013

(87) PCT Pub. No.: WO2012/061911
PCT Pub. Date: May 18, 2012

(65) Prior Publication Data
US 2013/0340113 A1    Dec. 19, 2013

(30) Foreign Application Priority Data

Nov. 12, 2010  (BR) ............................. 020100106005

(51) Int. Cl.
*C12N 15/82* (2006.01)
*C07K 14/415* (2006.01)

(52) U.S. Cl.
CPC ........ *C12N 15/8273* (2013.01); *C07K 14/415* (2013.01)

(58) Field of Classification Search
None
See application file for complete search history.

(56) References Cited

U.S. PATENT DOCUMENTS

2008/0127365 A1 * 5/2008 Sanz Molinero .... C07K 14/415
800/278

OTHER PUBLICATIONS

Agalou et al (Plant Mol Biol., 2008, 66: 87-103).*
GenBank GT013253 published 2009 (see alignment appended to office action).*
GenBank GT015128 published 2009 (see alignment appended to office action).*
Nobres et al (Tropical Plant Biology, 2016, 9(1): 50-62).*
UniProt Q651Z5.1 (Nov. 2008, cited in Office action).*
Lin et al (The Plant Journal, 2008, 55: 301-310).*
Ariel et al (Trends in Plant Science, 2007, 12(9): 419-426).*

* cited by examiner

*Primary Examiner* — Stephen Uyeno
(74) *Attorney, Agent, or Firm* — Sughrue Mion, PLLC

(57) ABSTRACT

The proposed innovation relates to the biotechnological improvement of plant species of commercial interest. More specifically, the present invention relates to the production of transgenic plants biotechnological with greater tolerance to water deficit and salt stress by means of the expression of a new gene of coffee (of the *Coffea Arabica* species), belonging to the HD-Zip family, and characterized by a homeodomain associated with a leucine zipper. The expression of this transcriptional factor is induced in leaves and roots of coffee plants subjected to various water deficit conditions (both moderate and severe); transgenic plants that over-express this gene inhibiting greater tolerance both to differ drought intensities and to high salt concentrations.

Figure 1:
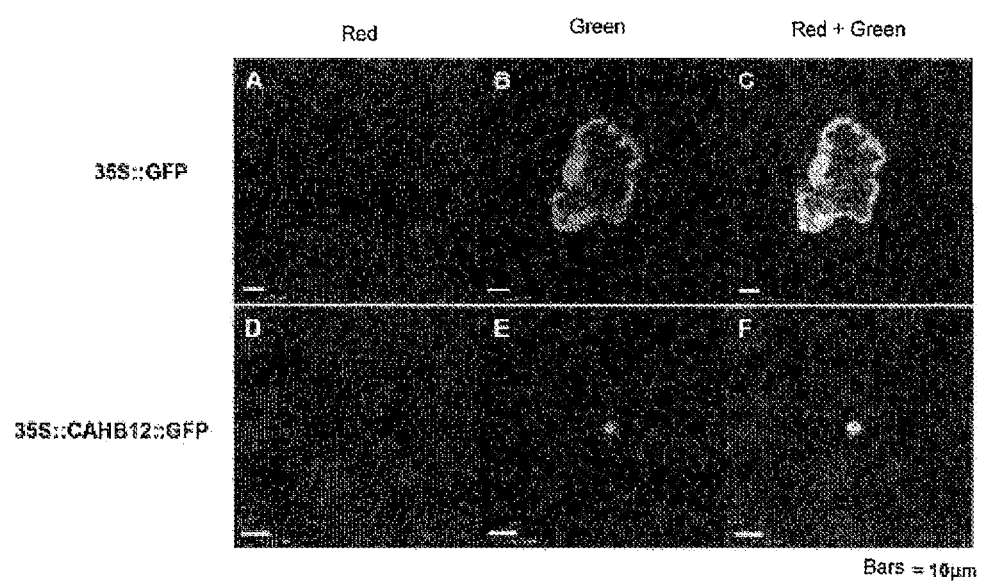

11 Claims, 9 Drawing Sheets
Specification includes a Sequence Listing.

Figure 10

SEQUENCE LISTING

<160> NUMBER OF SEQ ID NOS: 14

<210> SEQ ID NO 1
<211> LENGTH: 693
<212> TYPE: DNA
<213> ORGANISM: Coffea arabica

<400> SEQUENCE: 1

```
atggaacaaa caggctattt tgaacaagag cgctggaagc cttccaacaa gcacagccct    60
ttcccagttc cgaagagaaa gaggcgcaac aatgctaaga ggttcagtga tgaacaagtg   120
aagtcacttg agtccatgtt taatcgggag gcaaagcttg aaccaaggaa caagctgcag   180
ctggcaaaag atctaggcct gcagccgcgc caggtatcaa tctggtttca gaacaaaagg   240
gcgagatgga aatcaaagaa actagagcaa gaatatagag tactaaaagc gaatttcgat   300
gctctatgcc accaatttga agccttgaag aagaaaatg agtctctgct tgagcagttg   360
cacacactaa atggtgtgct ggaaaactcc aataagaggc agagcagtag caaggattca   420
aatgaaaatg cagagcatac agctccgcca aaaagagacg agcatcctga gcgcagagaa   480
gatgatgaga ggacaacaaa ggtgaatgtt gatggggtag gcgtaaatga acactttgga   540
aaggaagacc aagcaaattt tgatatcttg actgaacaag agagagtac atctgcatca   600 cgaaagccat ggtgcaatct tgtctcagat gggctcttgg atgaatcatg ttgcccttca   660
agttggtggg atttctcaga tggcctttgc taa                                693
```

<210> SEQ ID NO 2
<211> LENGTH: 230
<212> TYPE: PRT
<213> ORGANISM: Coffea arabica

<400> SEQUENCE: 2

```
Met Glu Gln Thr Gly Tyr Phe Glu Gln Glu Arg Trp Lys Pro Ser Asn
1               5                   10                  15

Lys His Ser Pro Phe Pro Val Pro Lys Arg Lys Arg Arg Asn Asn Ala
            20                  25                  30

Lys Arg Phe Ser Asp Glu Gln Val Lys Ser Leu Glu Ser Met Phe Asn
        35                  40                  45

Arg Glu Ala Lys Leu Glu Pro Arg Asn Lys Leu Gln Leu Ala Lys Asp
    50                  55                  60

Leu Gly Leu Gln Pro Arg Gln Val Ser Ile Trp Phe Gln Asn Lys Arg
65                  70                  75                  80

Ala Arg Trp Lys Ser Lys Lys Leu Glu Gln Glu Tyr Arg Val Leu Lys
                85                  90                  95

Ala Asn Phe Asp Ala Leu Cys His Gln Phe Glu Ala Leu Lys Lys Glu
            100                 105                 110

Asn Glu Ser Leu Leu Glu Gln Leu His Thr Leu Asn Gly Val Leu Glu
        115                 120                 125

Asn Ser Asn Lys Arg Gln Ser Ser Ser Lys Asp Ser Asn Glu Asn Ala
    130                 135                 140

Glu His Thr Ala Pro Pro Lys Arg Asp Glu His Pro Glu Arg Arg Glu
145                 150                 155                 160

Asp Asp Glu Arg Thr Thr Lys Val Asn Val Asp Gly Val Gly Val Asn
                165                 170                 175

Glu His Phe Gly Lys Glu Asp Gln Ala Asn Phe Asp Ile Leu Thr Glu
            180                 185                 190

Gln Gly Glu Ser Thr Ser Ala Ser Arg Lys Pro Trp Cys Asn Leu Val
        195                 200                 205

Ser Asp Gly Leu Leu Asp Glu Ser Cys Cys Pro Ser Ser Trp Trp Asp
    210                 215                 220

Phe Ser Asp Gly Leu Cys
225                 230
```

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide primer

<400> SEQUENCE: 3
caccatggaa caaacaggct a            21

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 4
gttctggagg catatgcact gg           22

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 5
tgtttaatcg ggaggcaaag              20

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 6
gcccttttgt tctgaaacca              20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 7
aagaaggaat tccccctgtg              20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 8
acctccacct ctcagagcaa              20

<210> SEQ ID NO 9
<211> LENGTH: 21
<212> TYPE: DNA
<213> ORGANISM: Artificial Sequence
<220> FEATURE:

```
<223> OTHER INFORMATION: Synthetic oligonucleotide primer

<400> SEQUENCE: 9
aggctgttgg gaaagttctt c                                           21

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 10
actgttggaa ctcggaatgc                                             20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 11
ccgaatgcca ttttttgtctt                                            20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 12
tccaaaccca gttgacttgc                                             20

<210> SEQ ID NO 13
<211> LENGTH: 24
<212> TYPE: DNA
<213> ORGANISM: Artificial Sequence
<220> FEATURE:
<223> OTHER INFORMATION: Synthetic oligonucleotide primer

<400> SEQUENCE: 13
ggaatccacg agacaaccta taac                                        24

<210> SEQ ID NO 14
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 14
aggaatcgtt cacagaaaat gtttc                                       25
```

USE OF THE COFFEE HOMEOBOX GENE CAHB12 TO PRODUCE TRANSGENIC PLANTS WITH GREATER TOLERANCE TO WATER SCARCITY AND SALT STRESS

FIELD OF THE INVENTION

The present invention relates to the plant biotechnological improvement of species of commercial interest. More specifically, the present invention relates to the production of transgenic plants that are more tolerant to the water deficit and salt stress, through the expression of a new coffee gene (sp. *Coffea arabica*), belonging to the HD-Zip family, characterized by the presence of leucine zipper associated homeodomain. The expression of this transcriptional factor is induced in coffee-plant leaves and roots subjected to different conditions of water deficit (moderate and severe) and, transgenic plants overexpressing this gene exhibit greater tolerance to both different levels of drought and high salt concentrations.

BACKGROUND OF THE INVENTION

Abiotic stresses, caused by too low or too high temperatures, by lack of water or by high concentrations of salts and heavy metals in soils, are responsible for great losses in agriculture, drastically reducing the production and generating losses that may exceed 50% (Boyer, 1982; Wang et al, 2003). In order to survive in such hostile environments, plants have developed a number of complex strategies that involve morphologic, physiologic and molecular alterations, in an attempt to become more tolerant (Nakashima et al., 2009; Verslues et al., 2000). Among abiotic stresses, drought has received growing attention, since, besides limiting the productivity, it has an important role in determining the distribution of the species in different ecosystems. The concern about the potential impact that climatic changes may cause on temperature and on the pluviometric patterns leads to the growing need to increase agricultural productivity (Ramalho et al, 2009). All over the world, about 70% of water available for consumption is used in agriculture and, although the irrigation is a strategy used to minimize the damages caused by lack of water, the irrigation system also has disadvantages such as the increase in the production cost and salinization of soils (Somerville & Briscoe, 2001). The classic improvement of agronomically important (e.g. *Coffea arabica*) with a view to develop such characteristics as flowering, higher productivity and greater resistance to pests and abiotic stresses (e.g. frosts and droughts), in spite of being successful, is also considered a slow development, which requires a huge demand for work and financial resources (Etienne et al., 2002).

Studies with transcription factors belonging to the homeobox family, more specifically to the HD-Zip family, reveal that these factors may be involved in modulating responses of plants to drought, controlling the plant development in such conditions (Deng et al., 2006; Dezar et al., 2005). The HD-Zip protein family is characterized by the presence of homeodomain (HD), coupled to an adjacent leucine zipper (LZ), which is important to the formation of homo- and heterodimers (Frank et al., 1998; Johannesson et at, 2001; Ruberti et al.; Sessa et al., 1993). The association or these two elements (HD and LZ) in a single protein is exclusive to plants, and this family represents, in number of members, from 40 to 50% of all the homeobox genes present in mosses to angiosperms. So far, four sub-DH-Zip protein subfamilies (HD-Zip I, II, III and IV) can be distinguished on the basis of the similarity of sequence and gene structure inside and outside the HD (Mukherjee et al., 2009). The expression of genes belonging specially to the HD-Zip I subfamily is generally modulated by environmental factors (e.g. light, low temperatures, salt and water stress), and its role in regulating the plant development in response to these stimuli may occasionally lead to phenotypes of greater tolerance to drought (Ariel et al., 2007).

U.S. Pat. No. 5,981,729 relates to a new gene of the homeobox family, isolated from the species *Arabidopsis thatiana*, which encodes the ATHB-12 transcription factor, related to the response to drought and to abscisic acid (ABA). Said gene may be cloned on expression factors to produce a recombinant DNA expression system, suitable for the transformation of plant cells and the production of transgenic plants that are more tolerant to drought. Said patent, however, does not mention or make any reference to any tolerance experiment with transgenic plants bearing said gene.

Patent WO 04/099365 describes an invention characterized by a gene isolated from *Helianthus annuus*, which encodes the HAHB-4 transcription factor, belonging to the DH-Zip family. The expression of the HAHB-4 gene is reduced by water deficit or by abscisic acid (ABA), and may be cloned in DNA constructs to transform host cells and plants. The transgenic plants that express the transcription factor gene are tolerant and resistant to water deficit and high salinity. In the present invention the new CAHB12 coffee gene also encodes a transcription factor of the HD-Zip family, expressed in leaves and roots of coffee plants of the species *Coffea arabica* cultivated in conditions of water deficit, exhibiting growing levels of expression, according to the severity of the stress experimented. Transgenic plants bearing this gene under control of the 35S promoter, which guarantees a constructive expression, that is, all the organs at high levels, exhibit greater tolerance to different conditions of water deficit, at different stages of development, as well as greater tolerance to salt stress. The levels of tolerance to salt stress of plants bearing the CAHB12 gene are even higher than those observed in plants bearing the HAHB4 gene, described in patent WO 04/099365. In the present study, besides the rate of germination in the presence of varied concentrations of NaCl (100 and 150 mM), measures of fresh weight have been evaluated, as well as the levels of lipid peroxidation mediated by water deficit monitored, through the rates of malonic aldehyde. Transgenic plants expressing the CAHB12 gene exhibited germination rages ranging from 20 to 45% higher than those of non-transgenic plants cultivated in the presence of 150 mM of NaCl. In patent WO 04/099365, the percentage of transgenic and non-transgenic plants germinated 46 hours after the beginning of the experiment was the same (100%). In the present invention, the plants belonging to the transgenic lines expressing the CAHB12 gene exhibited higher fresh weight measures than those observed for wild plants germinated in a culture medium containing 100 mM of NaCl. Besides, the level of lipid peroxidation remained virtually unchanged in two of the three transgenic lines tested, when cultivated in the presence of 100 mM of NaCl. In this context, the present invention may be used to impart greater tolerance to drought and salt stress of plants, further obtaining better performance with regard to salt stress than that observed and described in patent WO 04/099365.

The sequences with access number GT13253 and GT015128 were deposited at the public databank GenBank (National Center for Biotechnology Information), on Sep. 1, 2009, exhibiting, respectively, 89 and 92% identity with the CAHB12 gene. Although the article in which the sequences GT13253 and GT015128 are listed suggests the expression of these sequences in conditions of biotic and abiotic stress, this article has not been published yet, and to there is no proven experimental evidence, be it the expression of these transcripts in such situations or a greater tolerance of transgenic plants to water deficit and salt stress, when overexpressing such transcripts. In addition, there is no direct correlation between the above-cited sequences and the CAHB12 gene. The fact that these genes belong to the HD-Zip family alone is not sufficient to prove their efficiency in generating more tolerance phenotypes, as for example the ATHB-7 and ATHB-12 genes, which, in spite of not exhibiting an increased expression ion situations of water deficit, do not lead to a phenotype of greater resistance with respect to transgenic plants overexpressing these genes.

SUMMARY OF THE INVENTION

The objective of the present invention is to use the CAHB12 coffee gene, or a fragment thereof, for the production of transgenic coffee plants or related species, which are more tolerant to water deficit and to salt stress. The construct in pB2GW7 binary vector contains the nucleotide sequence coding for the CAHB12 protein fused to the 35S promoter, and may be directly used for the transformation of plants.

DETAILED DESCRIPTION OF THE INVENTION

Figure 10:
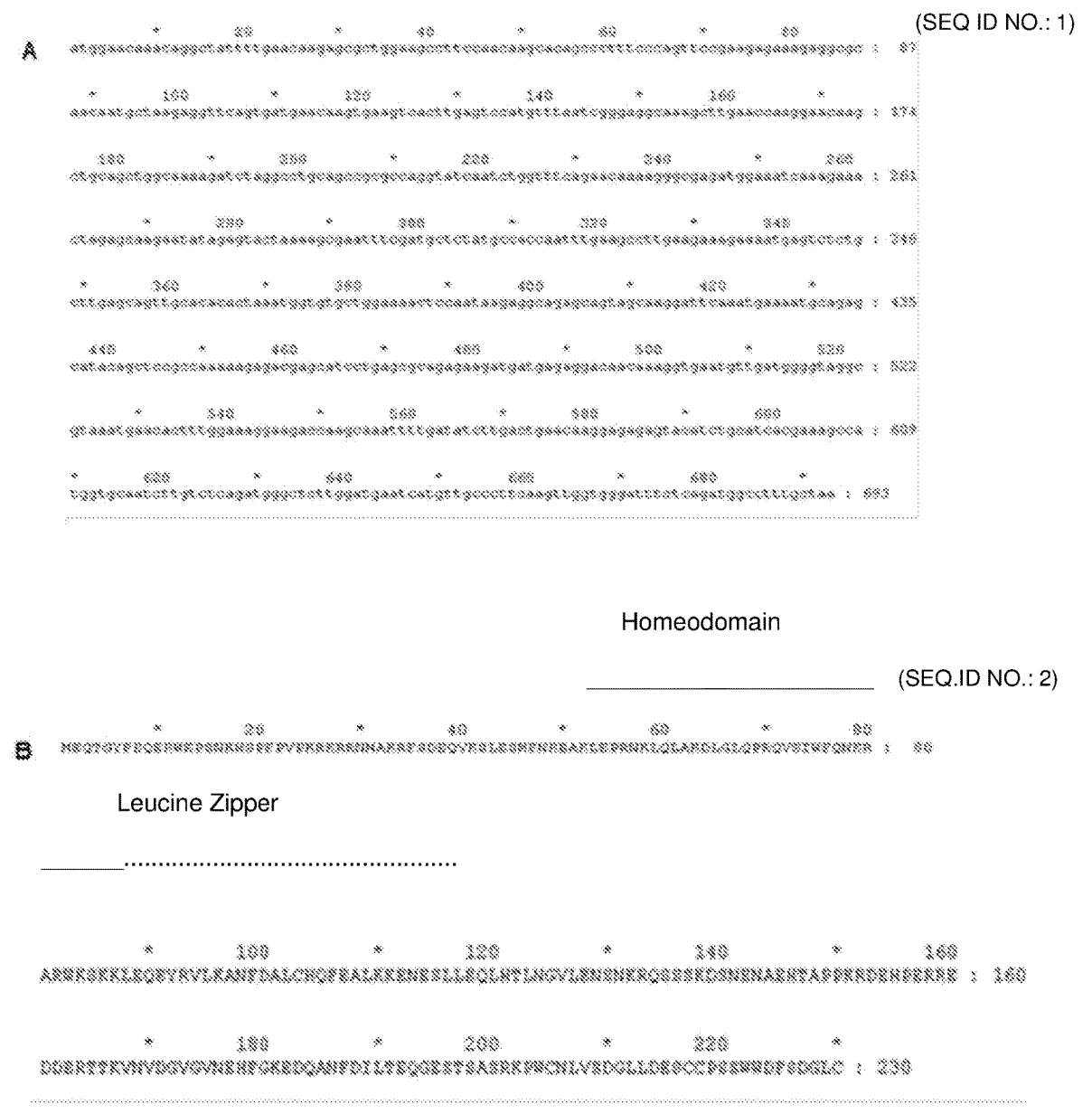

The CAHB12 gene was isolated from coffee through searches for homeobox genes that would exhibit their expression modulated in conditions of water deficit, using data made available by the Projeto Genoma do Café (Coffe Genome Project) project. The CAHB12 gene was classified as belonging to the HD-ZipI family, through the phylogenetic analyses by using the maximum likelihood method. The sequence corresponding to the complete cDNA of the CAHB12 gene was amplified by PCR reactions, and has 693 base pairs (ID1), giving rise to a protein formed by 230 amino acids (ID2). The OH (homeodomain) domain, comprised between the amino acids 53 and 87, and the Lz (leucine zipper) domain, comprised between the amino acids 88 and 116, are located in the region close to the N-terminal portion of the protein encoded by the CAHB12 gene (FIG. 10). The nucleus location of the CAHB12 protein was confirmed by transient expression tests by bombing coffee-plant leaves with gold particles coated with a plasmid construct containing the complete region coding for the CAHB12 protein and GFP (green fluorescent protein), fused trasnlationally, and under control of the 35S promoter (FIG. 1).

Figure 2:
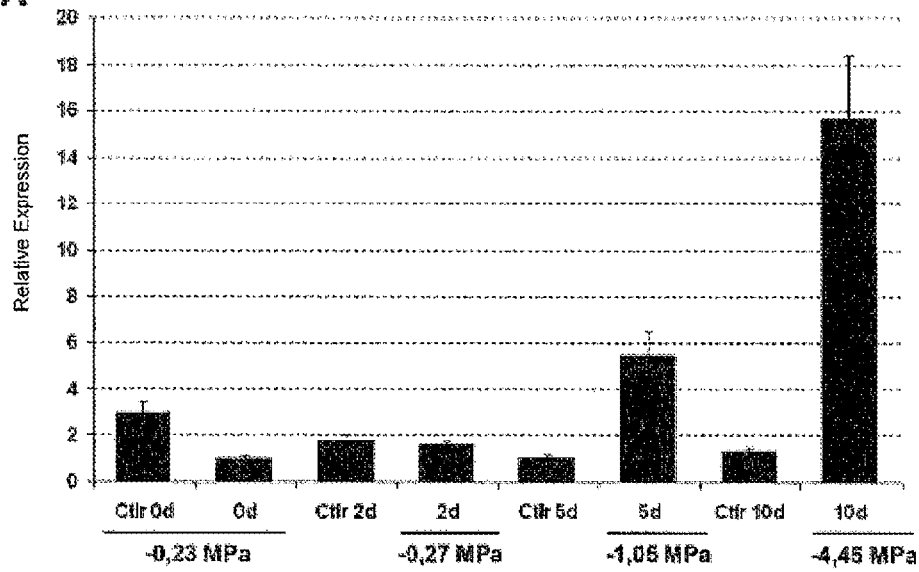
Figure 2:
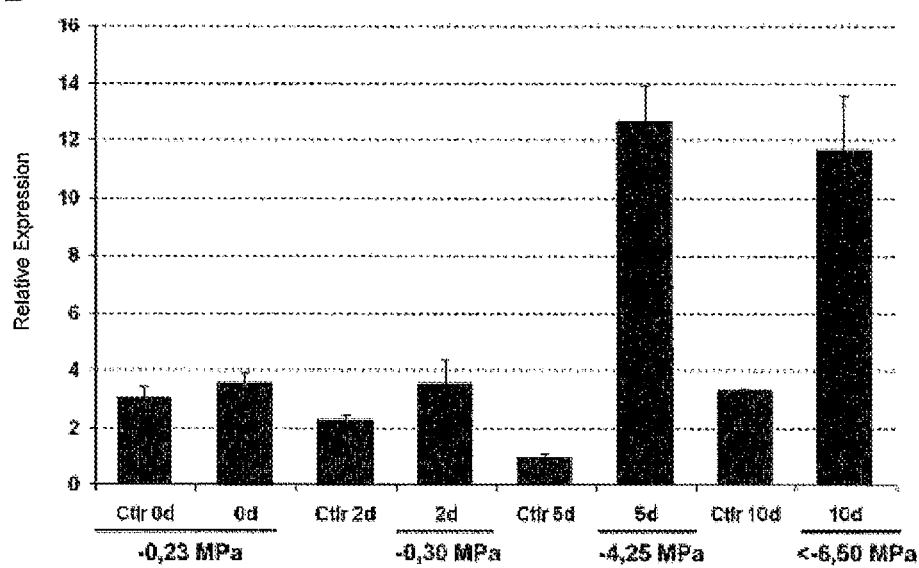
Figure 3:
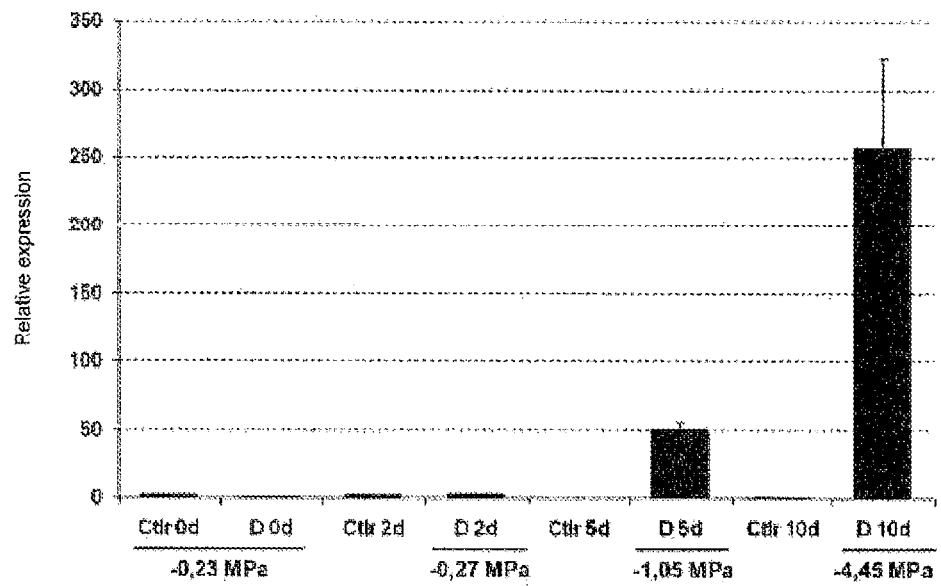

The expression pattern of the CAHB12 gene in coffee-plant leaves and roots was analyzed through PCR reactions in real time (RT-qPCR) in coffee plants of the species *Coffea arabica*, cultivars 'Catuai Vermelho IAC44' and 'Bourbom Amarelo IAC J10'. In normal conditions of cultivation in green house ($21\pm2°$ C. and natural photoperiod) the CAHB12 gene exhibited low levels of expression, having gradually induced in conditions of water deficit, in plants exhibiting measurements of water potential characteristic of stress (FIGS. 2 and 3). The experiments of water stress in greenhouses were carried out by using six months old coffee plants, on trays containing 20 plants each. The irrigation of the plants used as control was carried out by using 500 mL of water per tray, at 1-day intervals. The water potential ($\Psi w$) of each plant was measured in the period before sunrise with the aid of a Scholander pressure chamber. The water stress was induced by interrupting the irrigation for 10 days. Samples composed by totally expanded leaves (third pair) and side roots were collected in different induction periods (2, 5, and 10 days). The experiments were carried out in duplicate and each sample was composed by a material from 5 coffee-plants subjected to the same conditions. In both experiments, the expression profile of CAHB12 in conditions of water deficit exhibited the same tendency to induction. Samples of plants cultivated in control conditions were collected in the same periods of stress induction for comparison.

After 5 days induction, plants of the cv. 'Catuai Vermelho' (total of 5 plants) exhibited an average of $\psi w$ equal to $-1.05$ MPa ($\pm 0.92$ DP), whereas plants belonging to the cv. 'Bourbom Amarelo' exhibited an average of $-3.4$ MPa ($\pm 2.15$ DP). The same is true of the 10-day induction period, in which the plants exhibited averages of $\Psi w$ equal to $-4.45$ MPa ($\pm 1.30$ DP) and $<-6.5$ MPa, for the cvs. 'Catuai Vermeil' and 'Bourbom Amarelo', respectively, characterizing a severe water deficit (FIG. 2). However, for the 2-day induction period both cultivars exhibited averages of $\Psi w$ similar to that of the control plants, which remained approximately equal to $-0.23$ MPa ($\pm 0.10$ DP) for plants of the cv. 'Catuai Vermelho', and $-0.23$ MPa ($\pm 0.15$) for plants of the cv. Bourbom Amarelo'. Although the results obtained for both cultivars may not be directly compared, in both cases the plants exhibited $\Psi w$ values characteristic of stress only 5 days after the beginning of the experiments, coinciding with the expression induction of CAHB12, which demonstrates the induction specificity of this gene in drought conditions.

Figure 4:
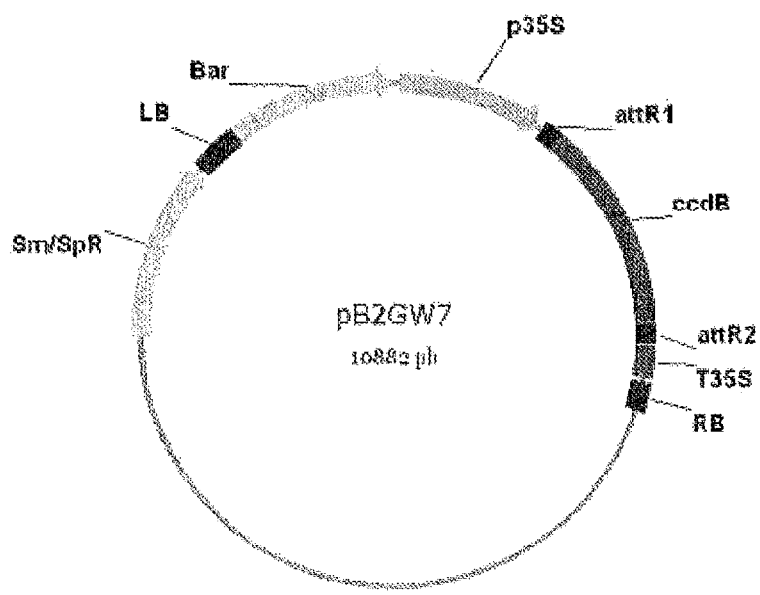

The obtainment of plants overexpressing the CAHB12 gene was carried out by cloning the complete cDNA of the gene under control of the 35S promoter in the vector Gateway® pB2GW7 (Karimi et al., 2002) (FIG. 4). Transgenic plants of the species *Arabidopsis thaliana* were transformed through the inflorescence infiltration system mediated by *Agrobacterium tumefaciens* (floral-dip) (Desfeaux et al, 2000). Three independent lines (A, B and D) of transgenic plants containing the CAHB12 coffee gene, segregating 3:1, were selected in a culture medium containing the glufosinate-ammonium soft Basta®. The selection of the transgenic plants until the third generation was carried out only through the segregation tests. Seeds and plants belonging to the T3 lines, produced by homozigous T2 plants, were then used for the tests for tolerance to water stress and salt stress. Studies of expression through RT-PCR were carried out with homozygous plants of generation T3 belonging to lines A, B and D (FIG. 5A). In a general way, transgenic plants did not exhibit any apparent phenotypic alteration. For the tests carried on plants, using a culture medium treated with PEG 8000, the malonic aldehyde rates (MDA) were monitored with a view to measure the level of stress undergone by the plants. The MDA is an indicator of the lipid peroxidation process mediated by consequent free radicals of water stress (Hodges et al., 1999).

Plantules belonging to the three transgenic lines overexpressing the CAHB12 gene produced less MDA than the wild plants of *A. thaliana* when subjected to the same conditions of stress on slide ($-1.2$ MPa) (FIG. 5B). In all the experiments, the D transgenic line was that which exhibited the lowest levels of MDA production, about 37 μmol/Kg, followed by lines B and A, which exhibited approximate values of 40 and 41 μmol/Kg, respectively. The measures observed for line B, however, were those that exhibited greater fluctuation, varying between 34 and 45 μmol/Kg.

Figure 6:
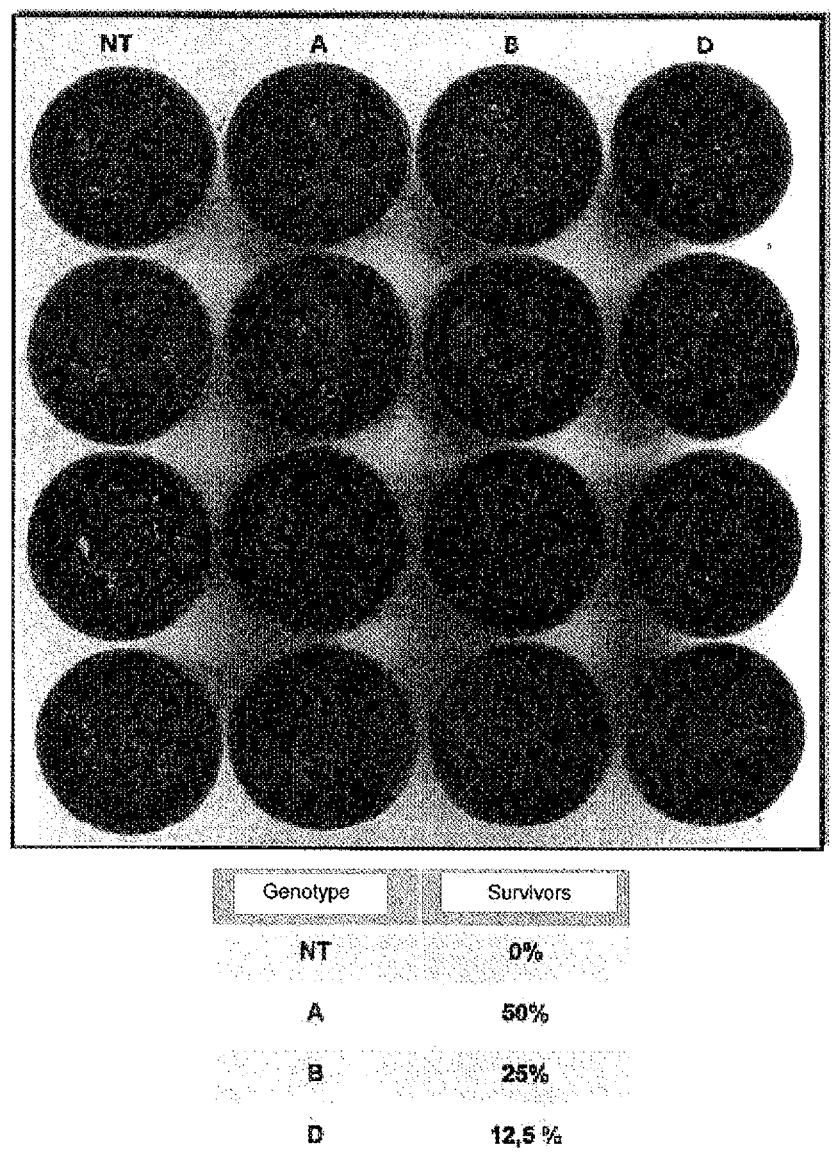
Figure 7:
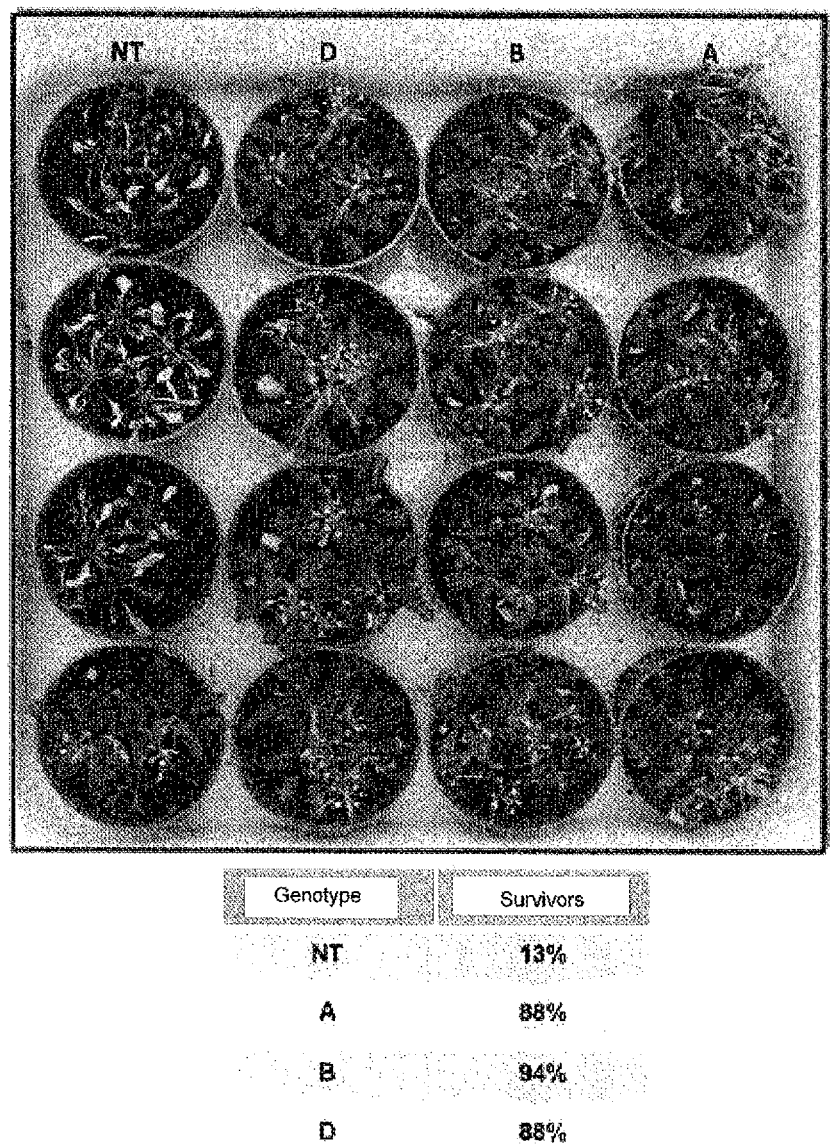

Two different types of tests for survival to water stress were carried out with plants in soil. In the first experiment, wild and transgenic plants were subjected to a severe water deficit. The rate of survival of the transgenic and wild plants was calculated two days after the rehydration of the trays. The transgenic plants always exhibited the same tendency during the tests, exhibiting an average survival rate around 29% higher than that observed for the wild plants (FIG. 6). In the second type of test for survival, one applied continuous water stress, in which the plants were subjected to a slower and gradual dehydration. For the tests of continuous stress, one used plants at the moment of transition of the reproductive phase to the fructification phase. Again, the transgenic plants exhibited an average survival rate, after rehydration, of about 87% higher than that observed for wild plants (FIG. 7).

Figure 8:
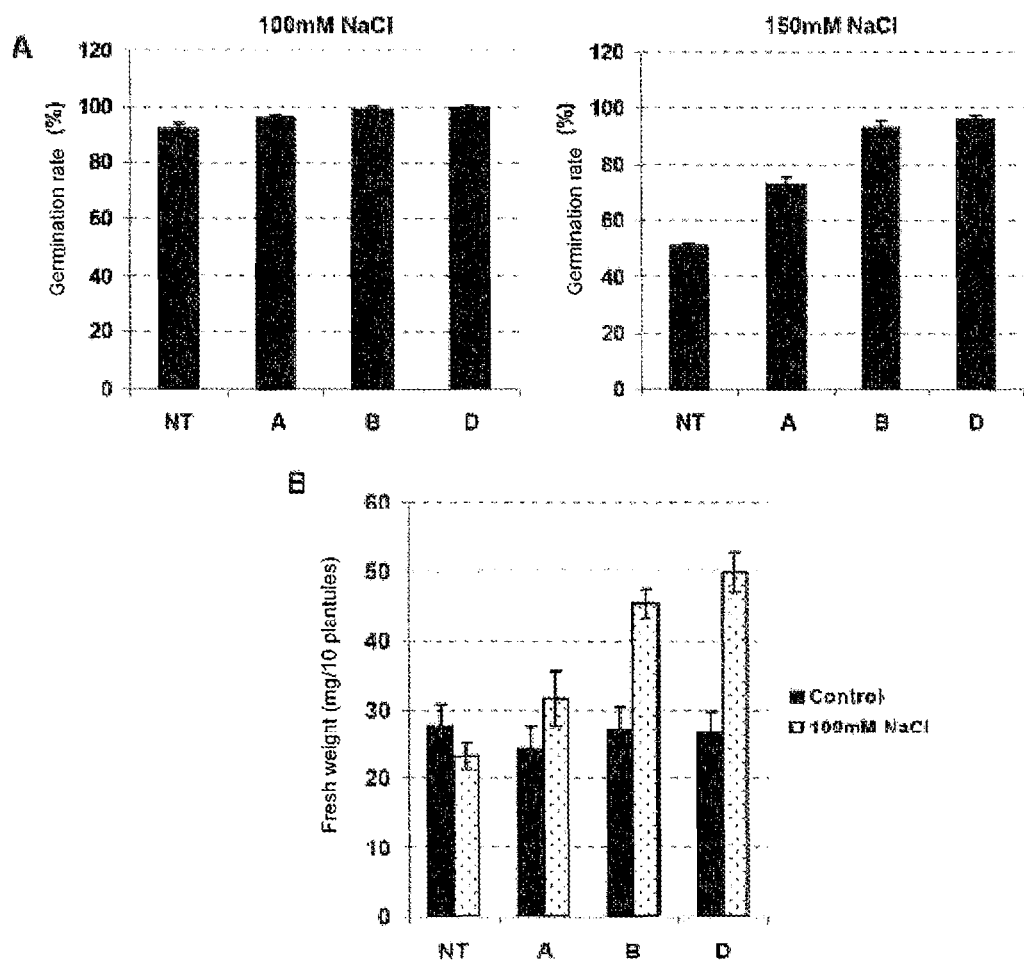

Tests for tolerance to salt stress were carried out on slides containing a culture medium supplemented with 10 and 150 mM of NaCl (Liu et al. 2009). The transgenic plants overexpressing the CAHB12 gene exhibited higher germination rates than the wild plants on slides containing 100 mM and 150 mM of NaCl (FIG. 8). The difference between the germination rates of wild and transgenic plants was more evident in the experiments carried on slides containing 150 mM of NaCl, than in the experiments carried out with 100 mM NaCl. In the two cases, however, the D line was the one that exhibited the lowest levels of inhibition of germination by salt stress (FIG. 8A).

Plants belonging to the three transgenic lines germinated in a medium containing 100 mM of NaCl exhibited higher fresh weight measures than those observed for the wild plants (FIGS. 8B and 9A). These measurements were carried out 15 days after transfer of the slides to the crowing chamber. The fresh weight of the transgenic plants under stress conditions was even higher than that observed for plants of the same line cultivated in control conditions. This difference was even more contrasting for plants belonging to lines B and D, which exhibited values of about 45 and 50 mg for every 10 plantules cultivated in a culture medium supplemented with 100 mM of NaCl, respectively, against 27 mg for every 10 plantules cultivated in control conditions.

The MDA measurements for the experiments carried out on slides containing 100 mM of NaCl exhibited greater tolerance of transgenic plants to salt stress, since the latter exhibited slower lipid peroxidation than those observed on wild plants (FIG. 9B). Tow independent experiments of salts stress on slides containing 100 mM of NaCl were carried out.

Summarizing, the CAHB12 gene is induced specifically in water deficit conditions on coffee-plant leaves and roots, indicating its importance in the response to this stress. Under control of the 35S promoter, the CAHB12 gene is capable of imparting greater tolerance to water deficit and salt stress of plants of the species *A. thaliana*, in different phases of their development.

Said invention can be used for producing transgenic plants belonging to different species of commercial interest. It should be further pointed out that the use of genes of the species itself in producing transgenic plants constitutes an advantage from the biotechnological point of view.

EXAMPLES

Example 1—Isolation and Cloning of the Full cDNA of the CAHB12 Gene on Bacterial and Plant-Expression Vectors The complete cDNA sequence of the CAHB12 homeobox was cloned by PCR amplification of the cDNA synthesized from the RNA of coffee-plants subjected to seven days without irrigation. The pairs of primers GW11116/11116mon, described in Table 1, were used for amplifying the CAHB12 gene. The PCR reactions were carried out in a total of 50 μL, containing 1 μL of cDNA diluted 1:2, MgSo4 1 mM, 0.4 mM of each dNTP, 0.1 μM of each primer, 10 μL of concentrated PCR Pfx 10× buffer, and 1 U of the Platinum® Pfx DNA Polymerase (Invitrogen) enzyme. Each reaction was incubated for 2 minutes at 94° C., followed by 35 15-second amplification cycles at 94° C., 30 seconds at 55° C., and 2 minutes at 68° C. Finally, a final extension step at 68° C. for 10 minutes was carried out. The band obtained exhibited the expected size of about 693 pb for the CAHB12 gene.

The PCR reactions were purified by using the DNA Clean & Concentrator™ kit (Zymo Research), according to the instructions of the manufacturer. The cDNA was then first cloned on the entre vector pENTR™ D-TOPO (Invitrogen) for subsequent recombination in expression vectors of the Gateway® system (Invitrogen). The binding reactions were carried out with 4 μL of the purified PCR reaction, 1 μL of salt solution (1.2M NaCl, 0.06M MgCl2) diluted 1:2, and 1 μL of the TOPO® vector, in a final volume of 6 μL. After 16 hours at room temperature (22-23° C.), 1 μL of the binding reaction was used for transforming cells of electrocompetent *Escherichia coli* XL1-Blue. The transformed bacteria were selected in a solid LB culture medium (peptone 10 g/L, yeast extract 5 g/L, NaCl 5 g/L, agar 15 g/L, pH 7.0) containing the canamycin antibiotic in the final concentration of 25 μg/mL. Then, the confirmation of the positive clones for the CAHB12 insert was carried out by colony PCR, using the same pairs of primers employed in the cDNA isolation reaction. Two clones containing the homeobox coffee gene were then chosen for sequencing.

The cloning of the CAHB12 on the Gateway pB2GW7 binary vector (Karimi et al., 2002) was carried out through recombination. In this vector, the cDNA of the homeobox gene was cloned under control of the 35S promoter region, though recombination between the regions attL1/attR1 and attL/attR2 of the entry vectors and destination vector, pENTR™ D-TOPO/pB2GW7, respectively. The recombination reactions were carried out in the following conditions: 1 μL of the LR Clonase™ II enzyme (Initrogen), 150 ng of the entry vector pENTR™ D-TOPO (containing the cDNA of each coffee homeobox), 150 ng of the destination vector Pb2GW7 and buffer TE(10 mM Tris-HCl, 1 mM EDTA) in a final volume of 5 μL. This mixture was incubated for 1 hour at 25° C. Then, 1 μL of a K 2 μg/μL proteinase solution was added to each previous reaction and a new incubation for 10 minutes at 37° C. was carried out. 2 μL of reaction were then used for transformation of electrocompetent *E. coli* XL1-Blu cells, and this time the positive clones were selected in a solid LB medium containing the antibiotic spectinomycin in the final concentration of 50 μg/μL.

The positive clones were then confirmed by colony PCR reactions, using the same pairs of primers described before in this item. The plasmid DNA of these clones was extracted and purified with the Wizard® Plus Minipreps DNA Purification System kit (Promega), and 1 μL of DNA diluted in the proportion of 1:100 was used for transforming electro-competent *Agrobacterium tumefasciens* GV3101 cells. The selection of the positive clones was carried out in a solid LB medium, containing 100 μg/mL of the antibiotics rifampicin and spectinomycin. After confirmation through colony PCR reactions, a clone containing the CAHB12 gene was selected for transformation of *A. thaliana* plants.

See Table 1

TABLE 1

PRIMERS USED FOR ISOLATING AND CLONING THE COMPLETE SEQUENCE OF THE cDNAs of the CAHB12 GENE

| Primers | Sequence | Orientation |
|---|---|---|
| GW11116 | 5'CACCATGGAACAAACAGGCTA-3' (SEQ ID NO.: 3) | Direct |
| 11116mon | 5'GTTCTGGAGGCATATGCACTGG-3' (SEQ ID NO.: 4) | Reversed |

Example 2—Analysis of the Expression Patter of the CAHB12 Gene in Coffee-Plant Leaves and Roots Under Water Deficit Conditions a. Plant Material The experiments with water stress in greenhouses were carried by using plants six month old of the species *C. arabica*, cvs. 'Catuai Vermelho IAC44' and 'Bourbon Amarelo IAC J10'. The plants were cultivated under conditions of controlled temperature (21±2° C.) and natural photoperiod, on trays containing 20 plants each. The irrigation of the plants was carried out by using 500 mL of water per tray, at 1-day intervals. The water potential ($\Psi w$) of each plant was measured in the period before sunrise with the aid of a Scholander pressure chamber. During the water deficit experiments, the plants remained covered overnight, and this protection was removed only at the moment when the $\Psi w$ measurements were carried out, in order to prevent interference of the perspiration rate with the values obtained. The water stress was induced by interrupting the irrigation for 10 days. Samples composed by totally expanded leaves (third pair) and side roots were collected in different induction periods (2.5 and 10 days). The experiments were carried out in duplicate, and each sample was composed by a material from 5 coffee plants subjected to the same conditions. Samples of plants cultivated in control conditions were collected in the same induction period of stress for comparison. All the samples collected were immediately frozen in liquid nitrogen and kept at −80° C. until the moment of RNA extraction.

b. Extraction of RNA and Synthesis of cDNA

Samples composed by coffee-plant leaves and roots were pulverized in liquid nitrogen, with the aid of pistil and pestle until a fine powder was achieved. About 100 mg of pulverized sample were resuspended in 500 μL of cooled (4° C.) Concert™ Plant RNA Reagent (Invitrogen), according to instructions from the manufacturer. After 5 minutes at room temperature, the samples were centrifuged for 2 minutes at 12000×g. The supernatant was transferred to a new tube, and 100 μL of a sodium chloride (NaCl) solution 5M and 300 μL of chloroform were added to the samples and mixed by inversion. Then, the samples were centrifuged at 4° C. for 10 minutes at 12000×g. The aqueous phase was recovered, and the total RNA was precipitated with an equal volume of isopropanol for 10 minutes at room temperature, followed by a centrifugation step at 4° C. for 10 minutes at 12000×g. The precipitate was washed with a 75% ethanol (EtOH) solution, dried at room temperature and dissolved in 30 μL of sterile distilled water.

In order to prevent contamination with gene DNA, the RNA samples were treated with DNAseI (Invitrogen) at 37° C. for 15 minutes, followed by two extractions with a phenol solution:chloroform:isoamyl alcohol (25:24:1) and precipitated with sodium acetate (NaOAc) 3M and EtOH 100%. The concentration and purity of the RNA were determined before and after the treatment with DNAseI with the aid of the NanoDrop™ ND-1000 spectrophotometer (Thermo Scientific). The integrity of the RNA was checked in 1% agarose gel.

The synthesis of cDNA was carried out by adding 50 μM of primers Oligo (dT24), and 10 mM of each desoxyribonucleotide 5'-triphosphate (dNTP) at 1 μg of total RNA. The mixture was incubated at 65° C. for 5 minutes, and cooled in ice briefly. 2 μL of First Strand Buffer 10×, 20 mM of dithio-threitol (DTT), and 200 units of enzyme Superscript III (Invitrogen) were added to the previous mixture until a final volume of 20 μL was achieved. After 1 hour at 50° C., the action of the enzyme was thermo-inactivated at 70° C. for 15 minutes.

c. RT-VCR Reaction

The pairs of primers for amplification of the CAHB12 gene were designed with the aid of the Primer3 program (Rozen & Skaletsky, 2000), using as a criterion the amplification of products with size ranging from 80 to 100 nucleotides, and annealing temperature of about 60° C. (Table 2). Analysis of the curve of dissociation of the amplified products, and runs in 1% agarose gel were carried out for confirmation of the amplification of a single PCR product. For normalization of the expression of the CAHB12 gene, one employed, as reference genes, the UBI9 (ubiquitin-like), S24 (ribosomal S24 protein) and GAPDH (glyceraldehydes-3-phosphate dehydrogenase C-2).

The polymerase chain reaction in real time (RT-qPCR) was performed in 96-well optical plates in the thermocycler Chromo 4 Real-time PCR Detector (BioRad), using the fluorophore SYBR® Green to monitor the synthesis of double-strands of DNA, 0.2 μM of each primer, 50 μM of each dNTP, 2 μL of 10× concentrate PCR Taq buffer (Invitrogen), MgCl$_2$ 3 mM, 1 μL of SYBR® Green (Molecular Probes) diluted in water (1:10,000), and 0.25 units of the enzyme Platinum Taq DNA Polymerase (Invitrogen) were added to 10 μL of cDNA diluted 1:50 in a final volume of 20 μL. The reactions were incubated at 94° C. for 5 minutes, followed by 40 amplification cycles of 15 seconds at 94° C., 10 seconds at 60° C., and 15 seconds at 72° C.

The values of the cutting cycle (cycle threshold—Ct) were converted by the program qBase v1.3.5 (Hellemans et al. 2007) into normalized relative quantities (NRQ) using the formula NRQ=$2^{-\Delta(\Delta CT)}$ in which 2 corresponds to amplification efficiency of 100%, ΔCt is the difference between the Ct of the sample with the lowest expression in the experiment and Ct of the sample in question, and ΔΔCt corresponds to the difference between the ΔCt of the sample in stress condition, minus the ΔCt of the sample in control condition. The normalization factor (NF) calculated from the expression of three reference genes (UBI9, S24 and GAPDH) was used for data normalization.

See Table 2

TABLE 2

PAIRS OF PRIMERS USED FOR GENE AMPLIFICATION CAHB12, UBI9, S24 AND COFFEE GAPDH.

| Gene: | Pair of primers (forward/reverse) | |
|---|---|---|
| CAHB12 | 5'-TGTTTAATCGGGAGGCAAAG-3'/ | (SEQ ID NO.: 5) |
| | 5'-GCCCTTTTGTTCTGAAACCA-3' | (SEQ ID NO.: 6) |
| UBI9 | 5'-AAGAAGGAATTCGCCCTGTG-3'/ | (SEQ ID NO.: 7) |
| | 5'-ACCTCCACCTCTCAGAGCAA-3' | (SEQ ID NO.: 8) |
| S24 | 5'-AGGCTGTTGGGAAAGTTCTTC-3'/ | (SEQ ID NO.: 9) |
| | 5'-ACTGTTGGAACTCGGAATGC-3' | (SEQ ID NO.: 10) |
| GAPDH | 5'-CCGAATGCCATTTTTGTCTT-3'/ | (SEQ ID NO.: 11) |
| | 5'-TCCAAACCCAGTTGACTTGC-3' | (SEQ ID NO.: 12) |

Example 3—Production of Transgenic Plants Over-Expressing CAHB12 Gene a. Plant Transformation and Selection of Transgenic Lines Plants overexpressing genes CAHB1 and CAHB12 were obtained by the infiltration system of inflorescence mediated by *Agrobacterium tumefaciens* (floral-dip) (Desfeux et al., 2000). For this, a colony isolated from *A. tumefasciens* GV3101 containing CAHB12 gene under the control of the 35S promoter (pB2GW7 vector) were grown for 48 hours at 28° C. under stirring for approximately 200 rpm in 2 ml of liquid LB medium (Peptone 10 g/L, yeast extract 5 g/L, NaCl 5 g/L, pH7.0), containing 100 μg/mL of the antibiotic rifampicin and 25 μg/mL of the antibiotic kanamycin, or 100 μg/mL of the antibiotic spectinomycin, depending on the construction to be transformed. This culture was used to inoculate 200 mL of liquid LB medium containing the same antibiotic present in the previous culture. After 16 hours of growth at 28° C. under stirring, the culture was centrifuged at 4000 rpm for 15 minutes. The supernatant was discarded, and the cells were resuspended in 200 mL of a solution containing 5% sucrose and 0.01% surfactant Silwet L-77. The flowers of adult plants of the species *A. thaliana* ecotype Columbia (Col-0) were dipped into this solution stirring gently. After 1 minute, the plants were placed in a horizontal position on a tray, and covered with a plastic film in order to maintain moisture. The next day, the plastic film was removed, and the plants were placed in upright position again. About 12 plants were transformed for each construction.

The seeds produced by the transformed plants were sterilized in a solution of 70% EtOH and 0.05% Tween 20 for 10 minutes and plated on solid MS medium (MS salts 4.6 g/L, sucrose 20 g/L, glycine 2 mg/L, nicotinic acid 5 mg/L pyridoxine HCl 0.5 mg/L thiamine-HCl 0.1 mg/L, agar 8 g/L, pH 5.8) (Murashige and Skoog, 1962) containing the herbicide glufosinate ammonium salt (Basta) at a final concentration of 10 μg/ml. The resistant transgenic lines were transferred to pots containing the substrate Plantmax® in a ratio of 3:1 (substrate:vermiculite) and thus cultured under light conditions (photoperiod of 18 hours of light/6 hours of darkness) and controlled temperature (22° C., ±2° C.). The seeds of the T0 generation of plants containing the CAHB12 gene in vector pB2GW7 were subjected to selection again with Basta in order to identify those lineages showing a 3:1 segregation of resistant and susceptible plants, indicating the presence of only one insertion T-DNA. 15-25 resistant plants of T1 generation of each lineage independently previously selected were transferred to pots containing substrate, and a new segregation test was conducted with the seeds produced by these plants, with the aim of identifying the heterozygous and homozygous T2 lineages. T2 plants cultured on plates being approximately 100% resistant to the herbicide or antibiotic used were transferred to pots containing substrate under the conditions mentioned above, and T3 seeds produced were then used for subsequent tolerance tests. For each segregation test 50 to 150 seeds were used.

b. Molecular Characterization of Lineages Over-Expressing Gene CAHB12

Approximately 100 mg of material of homozygous plants belonging to the T3 generation of transgenic lineages named A, B and D were collected in liquid nitrogen and used for RNA isolation according to the protocol described by Tai et al. with some modifications (Tai et al. 2004). The plant material was pulverized with the aid of metal microspheres and a Vortex mixer and resuspended in 500 μL extraction buffer[urea 6M, LiCl 3M, 0.01M Tris-HCl (pH8.0), 20 mM EDTA (pH8.0)]. Samples were mixed by inversion and 500 μL of a solution containing phenol:chloroform:isoamyl alcohol in the proportion 25:24:1 were added to the tube. Then, the samples were centrifuged at 12000×g, for 5 minutes, at 4° C. The supernatant was transferred to a new microtube and a new extraction with one volume of phenol:chloroform: isoamyl alcohol was carried out. To the supernatant recovered after centrifugation, as in the previous step, one volume of a solution containing chloroform:isoamyl alcohol (24:1) was added. The samples were centrifuged for 5 minutes at 12000×g (4° C.) and the RNA was precipitated by adding ⅒ of the volume of NaOAc 3M (pH5.2) and 1 volume of isopropanol to the supernatant. The tubes were kept on ice for 5 minutes, followed by a step of centrifugation at 12000×g for 10 minutes at 4° C. The precipitate was then washed twice with EtOH 70% and finally resuspended in 25 μL of sterile Milli-Q® water. The RNA integrity was checked on 1% agarose gel cDNA synthesis was performed as previously described in this section in item 3.4.2. PCR reactions were performed with primers GW11116 and 1116mon (Table 1) under the following conditions: 1 μL cDNA, 2.5 μL 10× PCR buffer concentrate, $MgCl_2$ 2 mM, 0.2 μM of each primer, 0.8 mM of each dNTP, and 1 U Taq DNA Polymerase (Invitrogen) enzyme in a total of 25 μL. Each reaction was incubated at 94° C. for 3 minutes, followed by 40 amplification cycles of 25 seconds at 94° C., 25 seconds at 59° C., and 55 seconds at 72° C. Finally, a final extension step at 72° C. for 10 minutes was carried out.

Expression of Actinll gene was used as internal control. For these amplification reactions, primers Ath_Actinll (5'-GGAATCCACGAGACAACCTATAAC-3') (SEQ ID NO.: 13) in forward orientation, and Ath_Actinll (5'-AG-GAATCGTTCACAGAAAATGTTTC-3') (SEQ ID NO.: 14) in reverse orientation were used, containing the same concentrations of reactants and cDNA described in the previous paragraph. Each reaction was incubated at 94° C. for 3 minutes, followed by 25 amplification cycles of 30 seconds at 94° C., 45 seconds at 62° C., and 45 seconds at 72° C. Finally, a final extension step at 72° C. for 10 minutes was carried out. The PCR products were checked on 1% agarose gels.

Example 4—Assays on Water Stress Tolerance of Transgenic Plants Over-Expressing CAHB12 Gene a. Assays on Water Stress Tolerance on Plates Treated with Peg 8000

Assays on water stress tolerance on plates treated with polyethylene glycol (PEG) 8000 were carried out according to the protocol described by van der Weele and others (van der Weele et al., 2000) with some modifications (Verslues & Bray, 2004) Plant seeds from of *A. thaliana* belonging to transgenic and wild lines were plated on MS culture medium containing half the concentration of salts without sucrose, and supplemented with 6 mM MES buffer (MS salts 2.3 g/L, glycine 2 mg/L, nicotinic acid 5 mg/L, pyridoxine-HCl 0.5 mg/L, thiamine-HCl 0.1 mg/L, agar 8 g/L, pH 5.7). 20 days after germination, seedlings were transferred to Petri dishes with standard size (100 mm diameter×20 mm height) containing 20 ml of MS culture medium modified as described above, previously treated with a solution of PEG8000 (MS salts 2.3 g/L, glycine 2 mg/L, nicotinic acid 5 mg/L pyridoxine HCl 0.5 mg/L thiamine HCl 0.1 mg/L, 6 mM MES buffer, PEG8000 550 g/L, pH 5.7). These plates were covered with 30 ml of PEG solution, in order to reduce the water potential of the culture medium to −1.2 MPa. After 16 hours of infusion, the PEG solution was completely removed, with the aid of a sterile pipette, and 30 seedlings of each wild and transgenic lines were transferred to the treated medium.

The plant material was collected 7 days after transfer to the medium treated with PEG. In total, two biological replicates were carried out for each transgenic line. In each experiment, two individual sets of seedlings were collected containing 15 individuals each. The amount of malondialdehyde (MDA) produced was subsequently monitored in an attempt to measure the level of lipid peroxidation of plants under stress. To avoid the effect of the transfer of plates in the MDA measurements, seedlings transferred to plates containing the culture medium not treated with PEG were used as control. The collected material was frozen in liquid nitrogen and kept at −80° C. until quantification of MDA.

b. Quantification of Malonic Aldehyde (MDA)

For the quantification of the production of MDA, the previously frozen material was first sprayed in liquid nitrogen, with the aid of metal microspheres and a Vortex mixer. Subsequently, 700 μL of trichloroacetic acid (TCA) 0.1%, previously cooled, were added. Extraction with TCA 0.1% was repeated one more time, and the samples were centrifuged at 12000×g, for 5 minutes, at 4° C. The supernatant was then divided into two tubes (600 μL each). The first tube contained 600 μL of solution composed of 20% TCA and butylated hydroxytoluene (BHT) 0.01%. The second tube contained the same volume (600 μL) of a solution composed of 20% TCA, 0.01% BHT and 0.65% thiabarbituric acid (TBA). The samples were mixed and the tubes incubated at 95° C. for 30 minutes. After this period, the samples were centrifuged at 12000×g, for 5 minutes, at 4° C. The absorbance values (ABS) of the tubes containing the solution of 20% TCA and 0.01% BHT were read on a spectrophotometer for the wavelengths 532 and 600 nm, while the absorbance values for the tubes containing 20% TCA, 0.01% BHT and 0.65% TBA, were read at wavelengths of 440, 532 and 600 nm. The 0.1% TCA solution was used to calibrate the readings of the apparatus.

The MDA/mL values of the processed tissue were estimated by the following formula (Hodges et al., 1999):

$$MDA(\mu mol/L) = [(A-B)/157000] \times 10^6,$$

where $A = [Abs532_{+TRA} - Abs600_{+TRA}] - (Abs532_{-TRA} - Abs600_{-TRA})]$.

and $B = [Abs440_{+TBA} - Abs600_{+TBA}) \times 0.0571]$.

These values were then converted into nmol/g using the formula:

MDA(μmol/L)×total volume of extraction (equals 1.4 mL)/fresh weight in Kg.

c. Survival Assays in Soil—Severe Water Stress

The assays on water stress tolerance in pots containing substrat were carried out in growth chambers under light conditions (photoperiod of 18 h of light/6 hours of dark) and controlled temperature (22° C., ±2° C.), with a relative unit of approximately 50%. Seeds from *A. thaliana* belonging to transgenic lines over-expressing CAHB12 and wild gene were sown in pots of the same size (8×7 cm) arranged in trays containing approximately the same amount of substrate (100 g) each (Dezar et al. 2005). The trays were, at first, watered to saturation (approximately 2 L of water) for 3 hours and after this period, the excess water was removed. In each pot, four seeds of the same genotype were sown. The trays were then covered with plastic film until the first pair of true leaves appeared, then the plastic was removed. From that moment, the trays were not watered until the symptom of constant wilt was observed in the wild plants, when rehydration of the trays was carried out. The number of survivors to the assay was checked two days after rehydration. All experiments were performed in duplicate, and analyzed as a whole, a total of 98 plants of the wild genotype, 64 plants of transgenic line A, 32 plants of transgenic line B, and 64 plants of transgenic line D.

d. Survival Assays in Soil—Continuous Water Stress

These assays were performed under the same conditions as item 3.9.3, but with a few modifications. After removal of the plastic film, the trays were watered normally for 30 days. From that moment, 1 mL of water was added daily to each pot until the symptom of constant wilt was observed in the wild plants, when rehydration of the trays was carried out. The number of surviving plants was recorded 2 days after rehydration. In this assay, the plants were in a later period of development, already at the stage of fruiting. Assays were carried out in duplicate and a total of 64 wild plants and 56 plants from each transgenic line were analyzed.

Example 5—Assays on Salt Stress Tolerance of Transgenic Plants Over-Expressing CAHB12 Gene The experiments of salt tolerance were carried out on plates containing solid MS culture medium supplemented with 100 and 150 mM of NaCl (Liu et at., 2009). Seeds of transgenic and wild plants were sown in aseptic conditions and kept at 4° C. for four days. After this period, the plates were transferred to a growth chamber where they were kept in conditions of light (18 hours of light/6 hours of darkness) and controlled temperature (22° C., ±2° C.). Germination rates were measured seven days after the transfer of plates to the growth chamber. Were considered positive for germination only those subjects who had the root fully inserted into the culture medium at the time of analysis. For the experiments performed in the presence of 100 mM NaCl, four plates containing 50 seeds each were analyzed, whereas only two plates containing 50 seeds were analyzed for the experiments carried out in the presence of 150 mM NaCl.

MDA measurements were carried out with seedlings germinated on medium containing 100 mM NaCl, 15 days after the transfer of the plates to a growth chamber. This experiment was carried out in duplicate, and for each, three sets of 10 seedlings were collected. These samples were immediately weighed and frozen in liquid nitrogen. Samples of plants grown on MS medium without added NaCl were used as control.

The sequences identified as SEQ ID NO:1 and SEQ ID NO:2 represent CAHB12 gene. (A) Nucleotide sequence encoding CAHB12 protein. (B) Amino acid sequence of CAHB12 protein. The position of the homeodomain is

BELOW IS THE DESCRIPTION OF EACH FIGURE

FIG. 1—Nuclear targeting of CAHB12 protein. Coffee leaves of C. arabica were bombarded with the following constructions: GFP protein under control of 35S promoter (A, B, C) and complete cDNA of CAHB12 gene fused to the GFP protein under control of 353 promoter (D, E, F). Transient expression was observed 24 hours after bombardment in confocal microscope, using the red fluorescence filters (A and D), green (B and E) and red and green (C and F). Bars=10 μm.

FIG. 2—Expression pattern of CAHB12 gene in lateral roots of plants of the species C. arahica, cultivars Catuai Vermelho (A) and Bourbom Amarelo (B). The expression values are shown on the y axis. Samples were collected at different induction times: 2 days (2d), 5 days (5d) and 10 days (10d). Samples from plants grown under control conditions (Ctr) were collected at each experimental time for comparison. Below the expression graphs the $\psi_w$ averages observed at the time of collecting the material are indicated. Error bar=2EPM (n=3).

FIG. 3—EXPRESSION PATTERN OF CAHB12 GENE IN LEAVES OF PLANTS OF THE SPECIES C. *arabica*, CULTIVARS 'CATUAI VERMELHO'. The expression values are shown on the y axis. Samples were collected at different induction times: 2 days (2 d), 5 days (5 d) and 10 days (10 d). Samples from plants grown under control conditions (Ctr) were collected at each experimental time for comparison. Below the expression graphs the $\psi_w$ averages observed at the time of collecting the material are indicated. Error bar=2EPM (n=3).

FIG. 4—Scheme of the destination vector pB2GW7 (Karimi at al., 2002). The pink arrows indicate the location of resistance genes for herbicide glufosinatc ammonium salt (Bar) and the antibiotics streptomycin (Sm) and spectinomycin (Sp). The position of the 35S promoter and terminator are indicated by the arrow and the green box, respectively. The ccdB region is indicated by the light blue box, between the two recombination regions attr1 and attR2. The red boxes indicate the T-DNA flanked by right border (RB) and left border (LB) regions.

Figure 5:
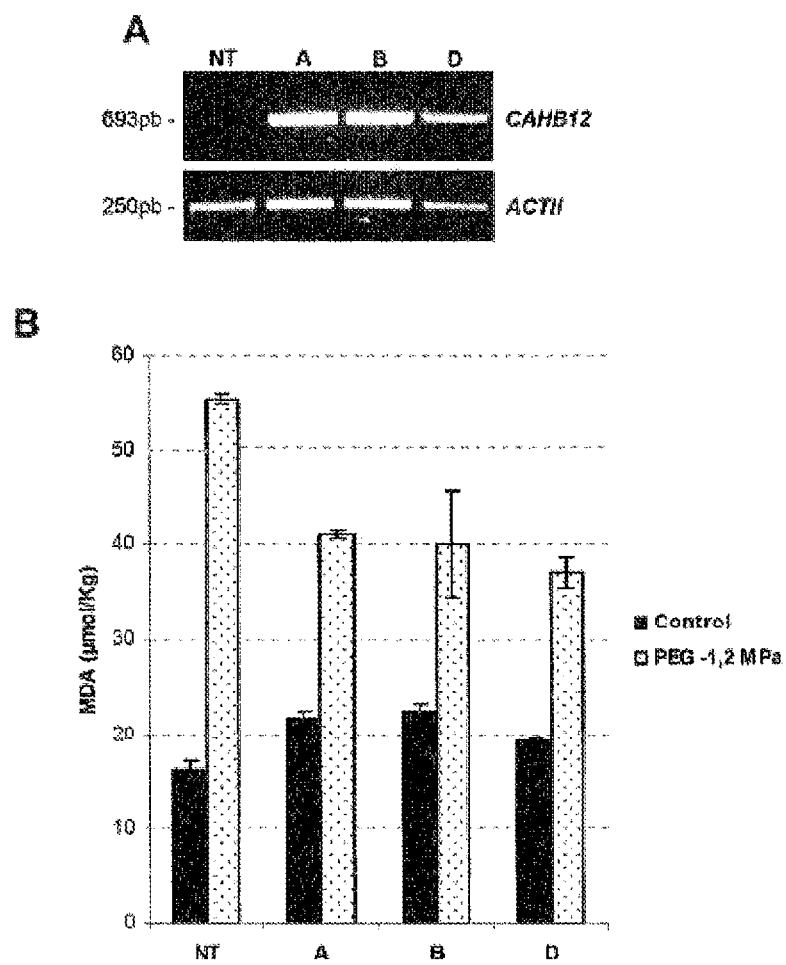

FIG. 5—(A) Detection of transcripts by RT-PCR for the CAHB12 gene in third generation homozygous plants of transgenic lines A, B and D. The level of expression of Actinall (ACTH) gene was used as internal control (indicated at the bottom of the figure). (B) Measurements of malonic aldehyde (MDA) after 7 days in culture medium treated with PEG8000 (-1.2 MPa). The error bars correspond to standard error (SE) obtained from two replicates of 15 seedlings each NT—Not transgenic FIG. 6—SURVIVAL ASSAYS TO SEVERE WATER STRESS Transgenic plants overexpressing CAHB12 gene and wild gene were subjected to severe water stress conditions, and rehydrated after observation of permanent wilting symptoms. In the top panel, the picture shows plants 2 days after rehydration. The table in the lower panel indicates the percentage (total=16 plants) the survival rate of plants after rehydration. NT—Not transgenic.

FIG. 7—Survival Assays to continuous water stress. In the top panel, the picture shows plants 2 days after rehydration. The table in the lower panel indicates the percentage (total=16 plants) the survival rate of wild and transgenic plants over-expressing the CAHB12 gene after rehydration. NT—Not transgenic.

| Genotype: | Survival |
|---|---|
| NT | 0% |
| A | 50% |
| B | 25% |
| D | 12.5% |

FIG. 8—CHARACTERIZATION OF TRANSGENIC PLANTS OVEREXPRESSING CAHB12 GENE IN SALT STRESS ASSAYS (A) Germination rates seven days after the transfer of plates to the growth chamber. The error bars correspond to the standard deviation (SD) calculated for four plates, each containing 50 plants for the experiments performed in culture medium containing 100 mM NaCl, and two plates, each containing 50 seeds, for experiments with 150 mM NaCl. (B) fresh weight observed in experiments with 100 mM NaCl. Each measurement was carried out for a set of 10 seedlings 15 days after the transfer of the plates to a growth chamber. The error bars correspond to the DP observed for a total of six measurements. NT—Not transgenic.

| Genotype: | Survival |
|---|---|
| NT | 13% |
| A | 88% |
| B | 94% |
| D | 88% |

Figure 9:
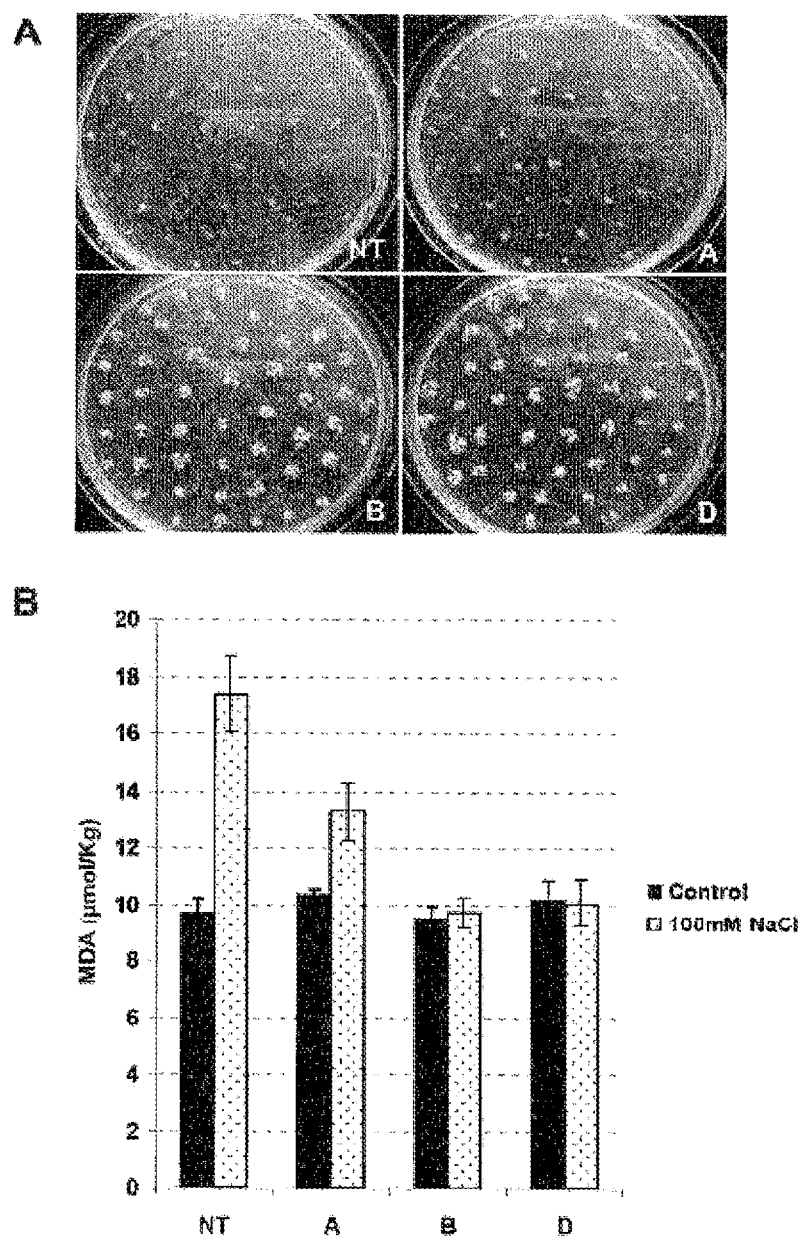

FIG. 9—TOLERANCE TO SALT STRESS IN PLANTS OVEREXPRESSING CAHB12 GENE (A) The effect of the salt treatment in wild and transgenic plants in culture medium containing 100 mM NaCl, 15 days after transfer of the plates to the growth chamber. (B) MDA measurements were carried out with germinated plants in culture medium containing 100 mM NaCl, 15 days after the transfer to the growth chamber. The error bars correspond to standard error (SE) obtained from 6 replicates containing 15 seedlings each. NT—Not transgenic.

FIG. 10—CAHB12 GENE.(A) Nucleotide sequence encoding CAHB12 protein. (B) Amino acid sequence of CAHB12 protein. The position of the homeodomain is indicated by the horizontal black bar above the sequence. The position of the leucine zipper is indicated by the dotted horizontal bar above the amino acid sequence.

The invention claimed is:

1. An isolated nucleic acid molecule comprising the nucleotide sequence of SEQ ID NO: 1 operably linked to a heterologous promoter sequence,
   wherein said nucleic acid, when expressed in host cells, confers greater tolerance of the host cells to water and salt stress as compared to cells not containing said nucleic acid.

2. A transgenic Want stably transformed with the nucleic acid molecule of claim 1, wherein said plant exhibits an increased tolerance to water and salt stress as compared to non-transgenic wild-type plants.

3. The nucleic acid molecule of claim 1, wherein said promoter is a 35S promoter.

4. A vector comprising the nucleic acid molecule according to claim 1.

5. A transgenic plant stably transformed with the vector of claim 4, wherein said plant exhibits an increased tolerance to water and salt stress as compared to non-transgenic wild-type plants.

6. The transgenic plant according to claim 5, wherein said plant is a monocotyledoneae.

7. The transgenic plant according to claim 5, wherein said plant is a dicotyledoneae.

8. A plant seed stably transformed with the nucleic acid molecule of claim 1.

9. A host cell stably transformed with the nucleic acid molecule of claim 1.

10. The cell of claim 9, wherein said cell is selected from the group consisting of a bacterial cell, a fungal cell, a plant cell and an animal cell.

11. A method for producing transgenic plants exhibiting an increased tolerance to water and salt stress as compared to non-transgenic wild-type plants, said method comprising stably transforming plant cells with the nucleic acid molecule of claim 1, and obtaining transgenic plants therefrom.

* * * * *